(12) United States Patent
Tubota

(10) Patent No.: US 8,479,365 B2
(45) Date of Patent: Jul. 9, 2013

(54) SYRINGE ASSEMBLY DEVICE

(75) Inventor: Nobutaka Tubota, Kyoto (JP)

(73) Assignee: Kyoto Seisakusho Co., Ltd., Kyoto (JP)

( * ) Notice: Subject to any disclaimer, the term of this patent is extended or adjusted under 35 U.S.C. 154(b) by 507 days.

(21) Appl. No.: 12/826,901

(22) Filed: Jun. 30, 2010

(65) Prior Publication Data

US 2012/0000046 A1 Jan. 5, 2012

(51) Int. Cl.
*B23P 19/04* (2006.01)
*B23P 19/02* (2006.01)
*B25B 27/14* (2006.01)
*B65B 43/42* (2006.01)
*B65B 1/04* (2006.01)
*A61M 37/00* (2006.01)
*A61M 1/00* (2006.01)

(52) U.S. Cl.
USPC .......... 29/240; 29/235; 29/238; 29/239; 29/281.1; 29/271; 141/144; 141/145; 141/147; 141/148; 141/27; 604/131; 604/152

(58) Field of Classification Search
USPC ............ 141/144, 145, 147, 148, 27; 604/131, 604/152; 29/235, 238, 239, 281.1, 271, 240
See application file for complete search history.

(56) References Cited

U.S. PATENT DOCUMENTS

2005/0282264 A1* 12/2005 Yu et al. .................... 435/283.1

FOREIGN PATENT DOCUMENTS

| JP | 2002-095746 | 4/2002 |
| JP | 2004-195556 | 7/2004 |

OTHER PUBLICATIONS

Machine Translation of "Method and apparatus for Capping, already and its preparation and apparatus" JP 09-299480A published Nov. 25, 1997 by Kazumi Iijima, Kazuyuki Yanase, and Toshio Takahashi.*
Machine Translation of "Assembling Arrangement" JP2004-195556 published Jul. 15, 2004 by Yamamota Kaoru.*

* cited by examiner

*Primary Examiner* — Lee D Wilson
*Assistant Examiner* — Nirvana Deonauth
(74) *Attorney, Agent, or Firm* — Morgan, Lewis & Bockius LLP

(57) ABSTRACT

A barrel support device supports a barrel rotationally about an axis of the barrel with the axis being arranged vertically and an opening of the barrel through which a plunger rod is inserted being directed upward. A chuck of a plunger rod support device holds the plunger rod in a first holding state in which the plunger rod is prevented from rotating about and sliding along its axis and inserts it into the barrel. Then, the chuck enters a second holding state in which the plunger rod is prevented from rotating about its axis but is not prevented from sliding along its axis. A load application device places a load acting downward on the plunger rod, and a rotation application device rotates the barrel in a direction in which the plunger rod is screwed into a gasket in the barrel.

3 Claims, 12 Drawing Sheets

SYRINGE ASSEMBLY DEVICE

BACKGROUND OF THE INVENTION

1. Field of the Invention

The present invention relates to a device that assembles syringes for use in medical practice.

2. Description of Related Art

In recent years, syringes for injecting drug solutions have often been provided as prefilled syringes that are previously filled with drug solutions. An example of the configuration of a syringe formed with a barrel and a plunger is shown in FIGS. 10A, 10B, 11A, 11B and 12.

The barrel 101 is a cylindrical component formed of synthetic resin; at one end thereof, a luer taper portion for the attachment of an injection needle is formed. The luer taper portion is covered with a sealing member 102 that is formed of rubber or soft synthetic resin. A shoulder portion that is formed in the process of narrowing the barrel to the thickness of the luer taper portion in a downward direction is a taper portion 101a. A flange 103 is formed at the other end of the barrel 101. The flange 103 is designed for the attachment of a grip member (not shown) underneath which first and second fingers are put; the flange 103 is not circular and is shaped to have a major axis and a minor axis. In FIG. 11A, an example of the flange 103 that is rectangular with rounded corners is shown; however, the flange 103 may have another shape such as an oval shape.

A gasket 104 formed of rubber or soft synthetic resin is inserted into the barrel 101. In the end face of the gasket 104 opposite the end face pointing to the luer taper portion, a screw portion 105 is formed in a position that coincides with the central axis of the barrel 101. The screw portion 105 is a right-hand female screw.

A plunger rod 106 is combined with the gasket 104. The plunger rod 106 is a component that is cross-shaped in cross section and is formed of synthetic resin; at one end thereof, a knob 107 for putting thereon the thick of a thumb is formed. On the other end of the plunger rod 106, a screw portion 108 that is screwed into the screw portion 105 of the gasket 104 is formed in a position of the central axis. The screw portion 108 is a right-hand male screw. By tightly screwing the screw portion 108 into the screw portion 105 of the gasket 104 within the barrel 101, the gasket 104 and the plunger rod 106 are integrally coupled to constitute the plunger 109 (see FIG. 12), and the barrel 101 and the plunger 109 constitute a syringe 100.

An automated line is used to manufacture the syringes 100. In the automated line, an assembly device is included that performs an operation of screwing the plunger rod into the gasket within the barrel. Examples of this type of assembly device are disclosed in patent documents 1 and 2.

In the syringe assembly device disclosed in patent document 1, while a plunger rod is so supported at a given height that it cannot be rotated, a barrel is rotated, and thus the plunger rod is screwed. The barrel is rotated by a belt mechanism that is obliquely provided with respect to its cylindrical surface. While the barrels are transported by an arrangement disc (wheel), labels are attached on them.

In the syringe assembly device disclosed in patent document 2, while a plunger rod is supported with a slider moving up and down due to the shape of a three-dimensional cam such that the plunger rod cannot be rotated, a barrel is rotated to perform screwing of the plunger rod. The barrel is rotated by a belt.

Patent document 1: JP-A-2002-95746
Patent document 2: JP-A-2004-195556

SUMMARY OF THE INVENTION

A belt that makes a friction contact with a barrel to transmit rotation also prevents the barrel from moving up and down freely. In the device disclosed in patent document 1, an angle at which the belt is obliquely arranged is needed to be precisely equal to the lead angle of the screw. Otherwise, since the belt does not follow the barrel raised by the screwing, it is likely that a screwing station is disadvantageously passed while the screwing rotation angle is insufficient. In other words, each time the lead angle of the screw is varied according to the type of syringe, it is necessary to adjust the angle at which the belt is obliquely arranged.

In the device disclosed in patent document 2, it is necessary to lower the plunger rod as the barrel is rotated. However, if the gasket is improperly positioned, the movement of the plunger rod that is lowered by the lead angle of the screw portion of the gasket differs from the movement of the slider that is lowered by the three-dimensional cam, and thus it is also likely that a screwing station is disadvantageously passed while the screwing rotation angle is insufficient.

In view of the forgoing, the present invention is designed, and has an object to provide a syringe assembly device that can completely and accurately screw a plunger rod into a gasket within a barrel.

According to a preferred embodiment of the present invention, there is provided a syringe assembly device for screwing a plunger rod into a gasket within a barrel, the syringe assembly device including: a barrel support device that supports a barrel rotationally about an axis of the barrel at a predetermined height with the axis being arranged vertically and an opening of the barrel through which the plunger rod is inserted being directed upward; a plunger rod support device that includes: a chuck which pinches the plunger rod and holds the plunger rod above the opening of the barrel with an axis of the plunger rod being arranged vertically; and a load application device which places a load on the plunger rod held by the chuck; and a rotation application device that rotates the barrel about the axis of the barrel. In the syringe assembly device, the rotation application device places the load acting in a downward direction of the axis on the plunger rod which is held by the chuck and whose end is inserted into the barrel, and, in this state, the load application device rotates the barrel in a direction in which the plunger rod is screwed into the gasket.

In this configuration, the load application device is used to place the load acting axially and downwardly on the plunger rod, and simultaneously the rotation application device is used to rotate the barrel and thereby screw the plunger rod into the gasket. Thus, as the screwing is being performed, the plunger rod is naturally lowered, and the movement of a screw portion of the gasket that lowers the plunger rod by a lead angle thereof does not differ from the actual movement of the plunger rod, resulting in complete and accurate screwing.

In the syringe assembly device configured as described above according to the preferred embodiment of the present invention, the chuck can enter a first holding state in which the plunger rod is prevented from rotating about and sliding along the axis of the plunger rod or a second holding state in which the plunger rod is prevented from rotating about the axis of the plunger rod but is not prevented from sliding along the axis, the plunger rod support device performs a first operation of lowering the chuck pinching the plunger rod in the first holding state to insert the end of the plunger rod into the barrel and a second operation of making the chuck enter the second holding state and making the load application device place the load acting axially and downwardly on the plunger rod, and the rotation application device rotates the barrel when the plunger rod support device performs the second operation.

In this configuration, when the chuck is in the second holding state in which the plunger rod is prevented from rotating about the axis of the plunger rod but is not prevented from sliding along the axis, the load application device is used to place the load acting axially and downwardly on the plunger rod, and simultaneously the rotation application device is used to rotate the barrel and thereby screw the plunger rod into the gasket. Thus, the screwing is performed without the plunger rod being hindered from lowered.

In the syringe assembly device configured as described above according to the preferred embodiment of the present invention, the barrel support device and the plunger rod support device are each provided in a plurality, and the barrel support devices and the plunger rod support devices are both spaced at equal angles on a circumference of a turret that rotates about a vertical axis, a chuck lifting device provided for the chuck includes: a three-dimensional cam arranged along a circling track of the plunger rod support device; and a chuck support stem being held by the turret such that the chuck support stem moves vertically along an undulation of the three-dimensional cam, the rotation application device may be supported by a rotary shuttle that moves back and forth on an arc track having the same center as the turret; and each of the turret, the rotary shuttle and the rotation application device is driven by an individual motor.

In this configuration, when parameters necessary to completely perform the screwing, such as the rotation angle of the barrel and the outer diameter of the barrel, are changed, the change can be easily and conveniently dealt with by changing the motor control program of the rotation application device.

According to the present invention, even if an error occurs in the position of the gasket within the barrel, it is possible to successfully screw the plunger rod into the gasket as desired.

DETAILED DESCRIPTION OF PREFERRED EMBODIMENTS

Figure 1:
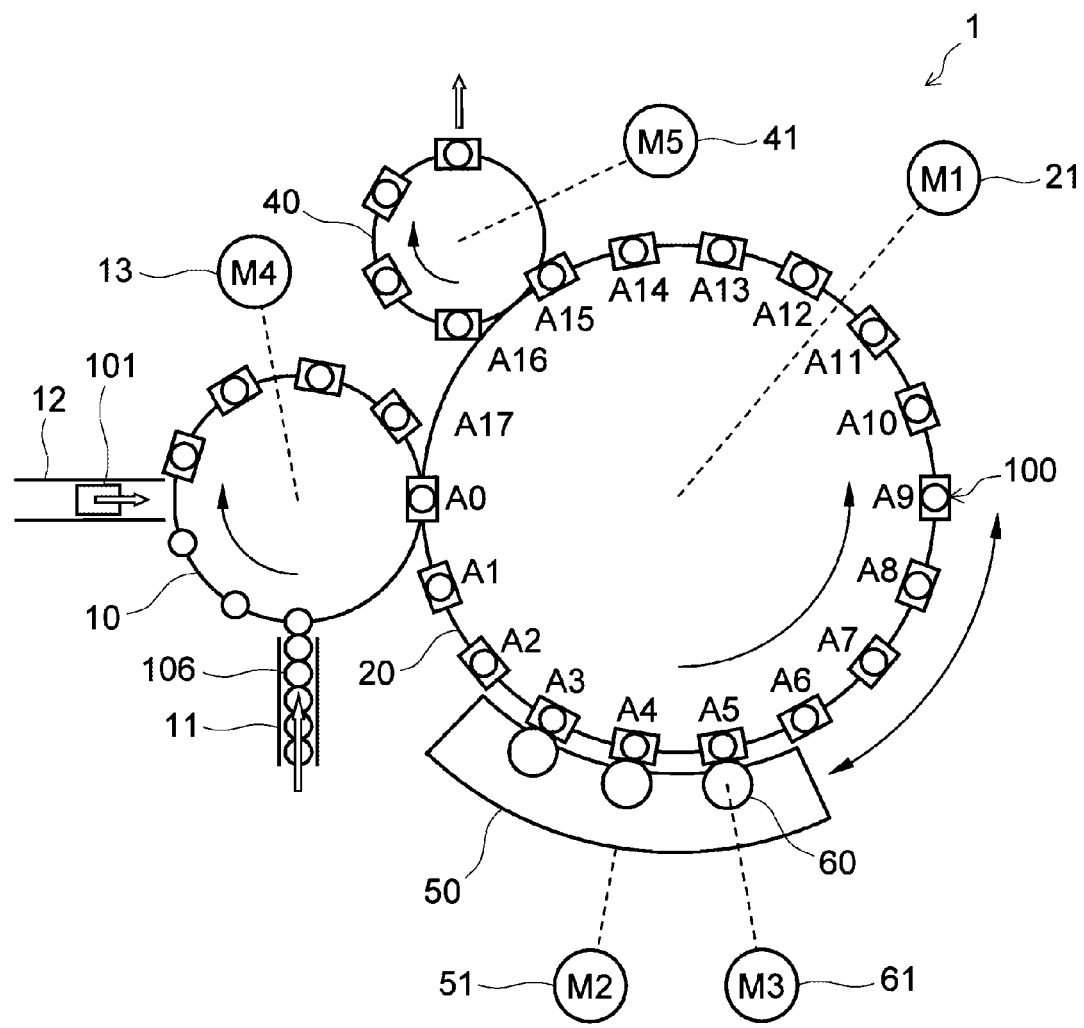
[FIG. 1] A plan view schematically showing the configuration of a syringe assembly device according to a preferred embodiment of the present invention.

The configuration of a syringe assembly device according to a preferred embodiment of the present invention will be described with reference to the accompanying drawings. The syringe assembly device 1 schematically shown in FIG. 1 has three turrets that are generally referred to star wheels. The three turrets are each configured as a rotary member that rotates about vertical shafts, and their circumferential speeds are set equal to each other. Among the three turrets, the first one is a component-receiving turret 10, the second one is a syringe assembly turret 20 and the third one is a relay turret 40. A rotary shuttle 50 that moves back and forth on an arc track having the same center as the syringe assembly turret 20 is combined with the syringe assembly turret 20.

Figure 10A:
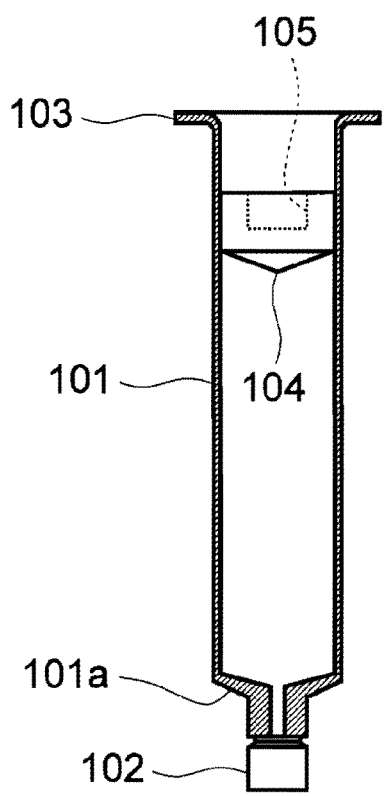
[FIG. 10A] A vertical cross-sectional view of a barrel for showing an example of the configuration of the syringe.
Figure 10B:
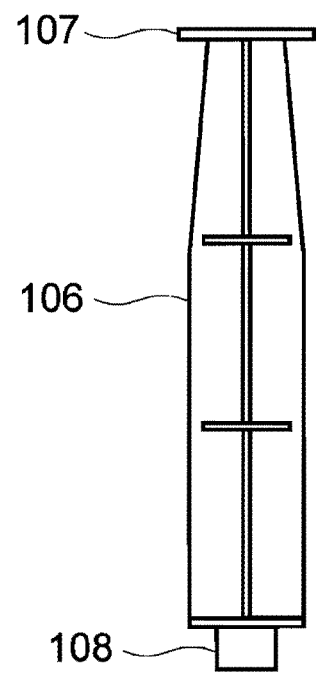
[FIG. 10B] A side view of the plunger rod that is combined with the barrel of FIG. 10A.
Figure 11A:
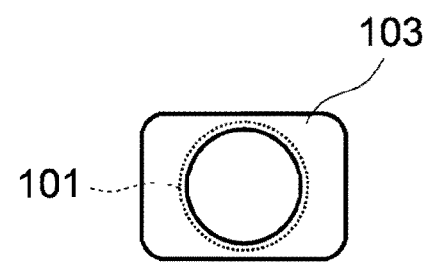
[FIG. 11A] A diagram of an end face of the barrel of FIG. 10A.
Figure 11B:
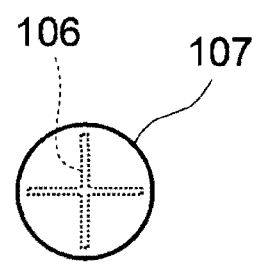
[FIG. 11B] A diagram of an end face of the plunger rod of FIG. 10B.
Figure 12:
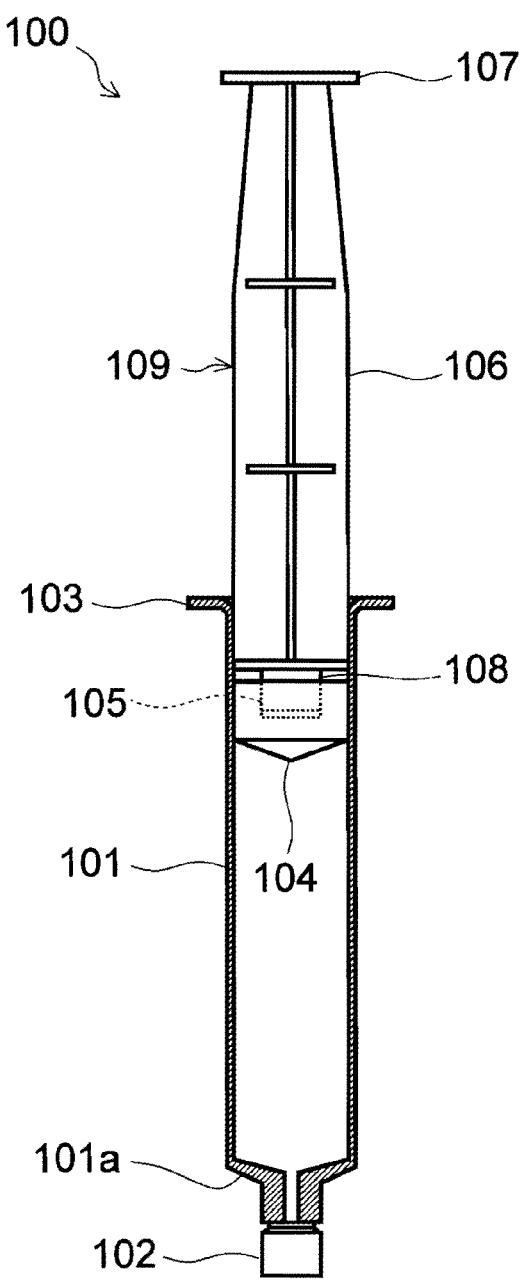
[FIG. 12] A vertical cross-sectional view of the syringe in an assembled state.

The component-receiving turret 10 receives plunger rods 106 shown in FIGS. 10B and 11B from a linear feeder 11, receives barrels 101 shown in FIGS. 10A and 11A from a linear feeder 12 and aligns them along a vertical axis to feed them to the syringe assembly turret 20. During a time the syringe assembly turret 20 transports the barrels 101 and the plunger rods 106 to the relay turret 40, a rotation application device 60 mounted on the rotary shuttle 50 moving along with the syringe assembly turret 20 rotates the barrels 101, and thus the plunger rods 106 are screwed into gaskets 104, with the result that syringes 100 are assembled. This mechanism will be described in detail later. The assembled syringes 100 are transferred from the syringe assembly turret 20 to the relay turret 40, and are then transferred from the relay turret 40 to a conveyer (not shown) in a label attachment line.

The component-receiving turret 10 is driven by a motor 13; the syringe assembly turret 20 is driven by a motor 21; the rotary shuttle 50 is driven by a motor 51; the rotation application devices 60 is driven by a motor 61; and the relay turret 40 is driven by a motor 41. The motors 51 and 61 are servomotors. The motors 13, 21 and 41 can be normal induction motors. A combination of all or some of the motors 13, 21 and 41 may be replaced by a single motor, and the rotation of the single motor may be distributed to the turrets and conveyer with power transmission means such as a gear train and a timing belt.

The motor 13, the motor 21 and the motor 41 continuously rotate the component-receiving turret 10, the syringe assembly turret 20 and the relay turret 40, respectively. The motor 51 moves the rotary shuttle 50 back and forth along the arc track. A mechanism that transmits power of the motor 51 to the rotary shuttle 50 for shuttle movement of the rotary shuttle 50 can be, for example, combination of an arc-shaped rack fixed to the rotary shuttle 50 and a pinion that engages the rack and is driven by the motor 51; however, the present invention is not limited to this mechanism.

Figure 2:
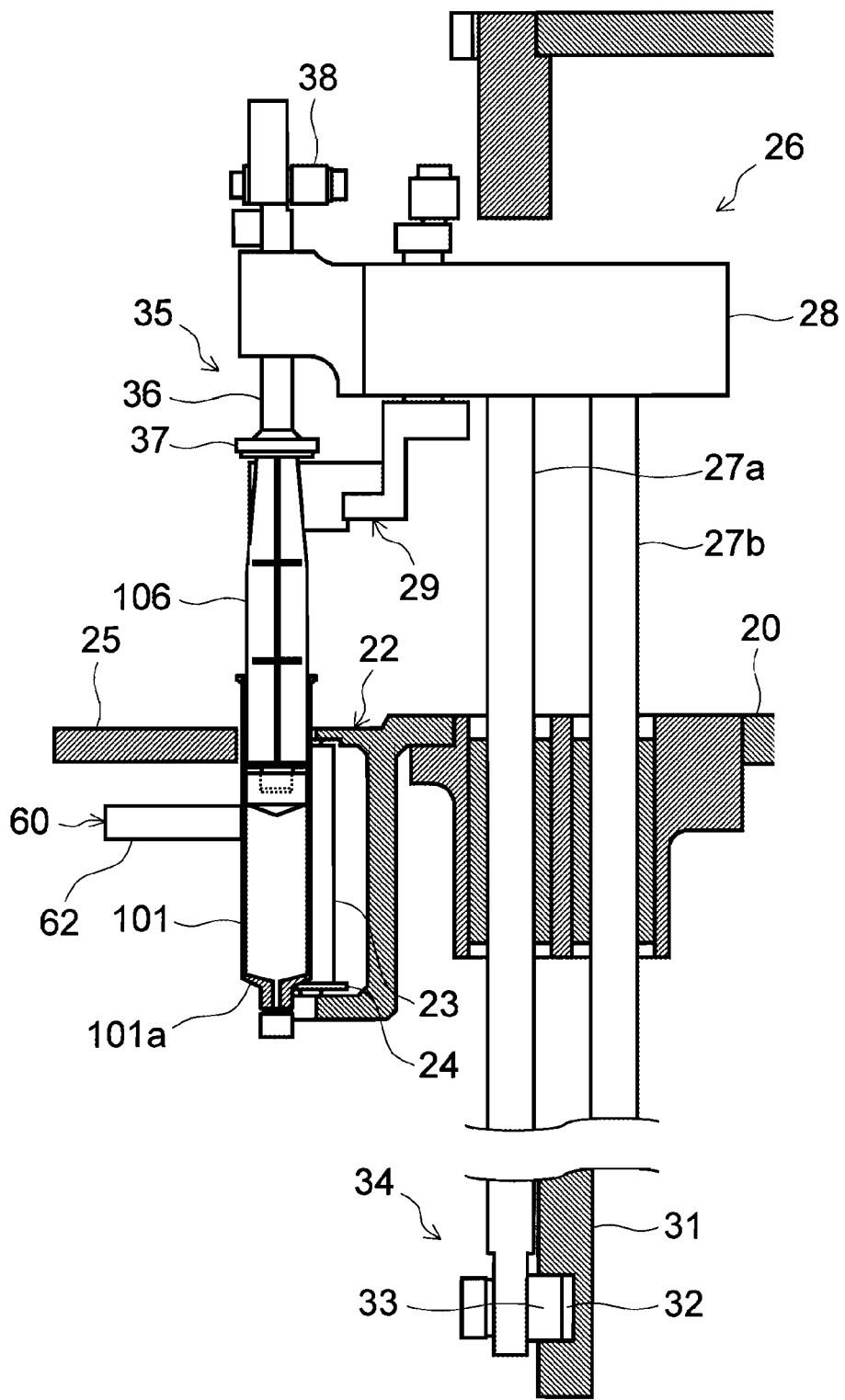
[FIG. 2] A cross-sectional view of part of a barrel support device and a plunger rod support device.

On the circumference of the syringe assembly turret 20, a total of eighteen barrel support devices 22 shown in FIG. 2 are spaced at equal angles. The barrel support device 22 supports a barrel 101 rotationally about an axis of the barrel 101 at a predetermined height with the axis of the barrel 101 being arranged vertically and an opening of the barrel 101 through which the plunger rod 106 is inserted being directed upward.

Figure 6:
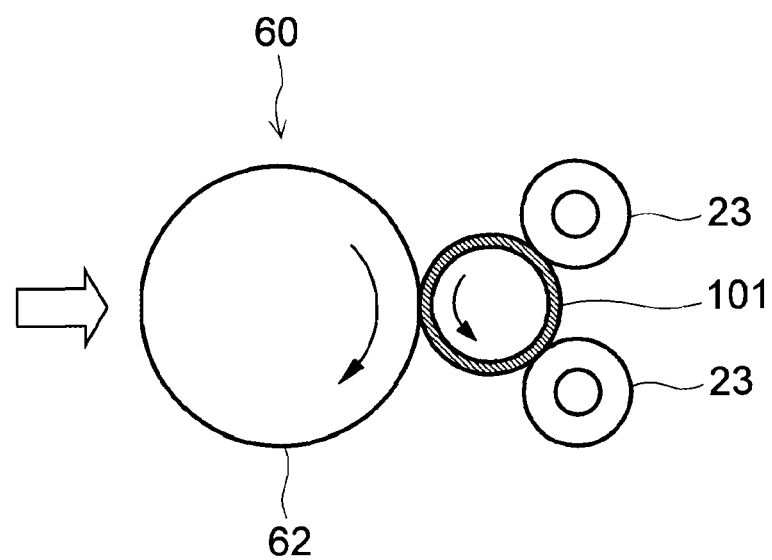
[FIG. 6] A horizontal cross-sectional view schematically showing the configuration of a rotation application device.

The barrel support device 22 includes backup rollers 23 that support a cylindrical surface of the barrel 101. The backup rollers 23 are supported rotationally about a vertical axis, and neighboring two are paired, as shown in FIG. 6. A flange 24 formed on the lower end of the backup roller 23 receives the taper portion 101a of the barrel 101, and thus the barrel 101 is held at the height.

If in the barrel 101, the shoulder portion, formed to narrow the barrel to the thickness of the luer taper portion, has a surface perpendicular to the barrel axis, the height of the barrel 101 is constant when the shoulder portion is received by the flange. However, since, in this embodiment, the shoulder portion is the taper portion 101a, it is not certain as to what part of the tapered surface the flange 24 comes in contact with. Thus, variation in the height of the barrel 101 is a given. Hence, if labels are attached to the barrels 101 while the syringe assembly turret 20 transports the barrels 101, as in the case of patent document 1, it is impossible to prevent variations in the location where the label is attached. To overcome this problem, label attachment means is not provided in the syringe assembly turret 20, but provided in another location.

An arc-shaped fixed guide 25 is provided outside the syringe assembly turret 20; this fixed guide 25 prevents the barrel 101 from coming off the backup roller 23. A clearance of about 0.5 mm is provided between the fixed guide 25 and the barrel 101.

In the syringe assembly turret 20, plunger rod support devices 26 are arranged to form pairs with the barrel support devices 22. The plunger rod support device 26 is provided with: two chuck support stems 27a and 27b that penetrate the syringe assembly turret 20 vertically and that can slide vertically; a deck 28 that is supported on the upper ends of the chuck support stems 27a and 27b; and a chuck 29 that is supported by the deck 28. The chuck 29 holds the plunger rod 106 in a vertical state, and arranges it above the opening of the barrel 101 held by the barrel support device 22.

Figure 3:
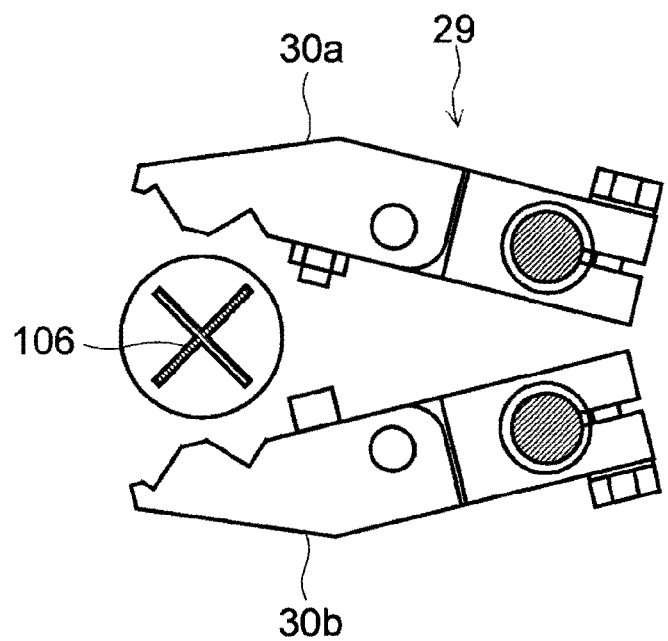
[FIG. 3] A plan view of a chuck in a full-open state.
Figure 4:
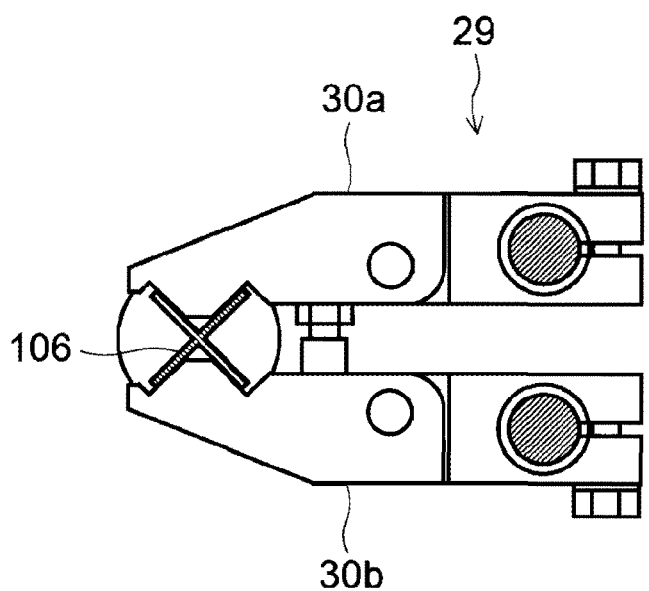
[FIG. 4] A plan view of the chuck in a first holding state.
Figure 5:
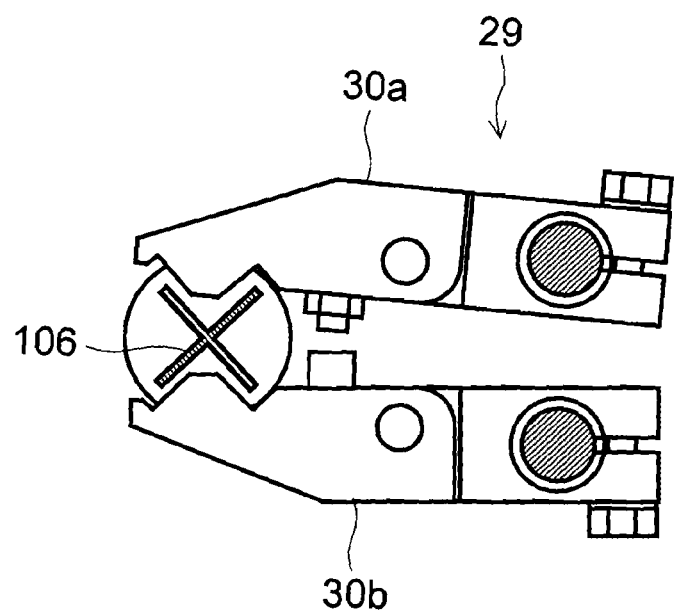
[FIG. 5] A plan view of the chuck in a second holding state.

As shown in FIGS. 3 to 5, the chuck 29 has a pair of fingers 30a and 30b, and the fingers 30a and 30b are closed to pinch the plunger rod 106 between both sides. In the opposite surfaces of the fingers 30a and 30b, recesses corresponding to the cross-shaped cross section of the plunger rod 106 are formed; as shown in FIGS. 4 and 5, the fitting of the cross-shaped cross section into the recesses prevents the plunger rod 106 from rotating about its axis.

With an unillustrated power source, the chuck 29 can be opened at three angles. First, as shown in FIG. 3, in a full-open state where the fingers are fully open, the fingers 30a and 30b are far away from the plunger rod 106, and the plunger rod 106 can freely rotate about the axis and move along its axis with respect to the chuck 29. Second, as shown in FIG. 4, in a first holding state where the fingers 30a and 30b pinch the plunger rod 106 from both sides, the plunger rod 106 is prevented from rotating about its axis and is also prevented from sliding along its axis with respect to the chuck 29. Third, as shown in FIG. 5, in a second holding state where the fingers 30a and 30b are slightly opened as compared with the first holding state, the plunger rod 106 is also prevented from rotating about its axis but can slide along the axis with respect to the chuck 29.

The plunger rod support device 26 is moved vertically by a three-dimensional cam 31 arranged along its circling track. The three-dimensional cam 31 is a ring-shaped member that is arranged coaxially with an unillustrated rotary shaft of the syringe assembly turret 20, and is attached to an unillustrated table supporting the syringe assembly turret 20. A cam groove 32 is formed in the outer circumferential surface of the three-dimensional cam 31, and a cam follower roller 33 attached to the lower end of the chuck support stem 27a engages with the cam groove 32. The chuck support stem 27a is moved vertically according to the shape of the cam groove 32. The three-dimensional cam 31 and the chuck support stem 27a constitute a chuck lifting device 34.

The plunger rod support device 26 includes a load application device 35. The load application device 35 is provided with: a pressure stem 36 that vertically penetrates the deck 28 of the plunger rod support device 26 and being capable of sliding vertically; a disc-shaped pressure head 37 fixed to the lower end of the pressure stem 36; and a cam follower 38 attached to the upper end of the pressure stem 36. In part of the circling track of the load application device 35, a three-dimensional cam 39 (see FIG. 7) on which the cam follower 38 rides is provided; the pressure stem 36 is moved vertically along undulations of the cam surface of the three-dimensional cam 39 (the upper surface of the three-dimensional cam 39).

The rotation application device 60 mounted on the rotary shuttle 50 has three combinations of the motor 61 and a roller 62 rotated by the motor 61. The rollers 62 are spaced at angles equal to the angles at which the barrel support devices 22 are spaced. The roller 62 makes contact with the outer circumferential surface of the barrel 101 supported by the barrel support device 22 to rotate the barrel 101.

An operation of assembling the syringes is performed as follows. A combination of the barrel support device 22 and the plunger rod support device 26, which is arranged on the circumference of the syringe assembly turret 20, sequentially passes through the total of eighteen angular positions (A0 to A17) set spaced at equal angles. At the angular position A0, the syringe assembly turret 20 and the component-receiving turret 10 intersect; the syringe assembly turret 20 and the relay turret 40 intersect between the angular position A15 and the angular position A16. The fixed guide 25 is arranged to cover the section from the angular position A0 to the angular position A15.

Figure 7:
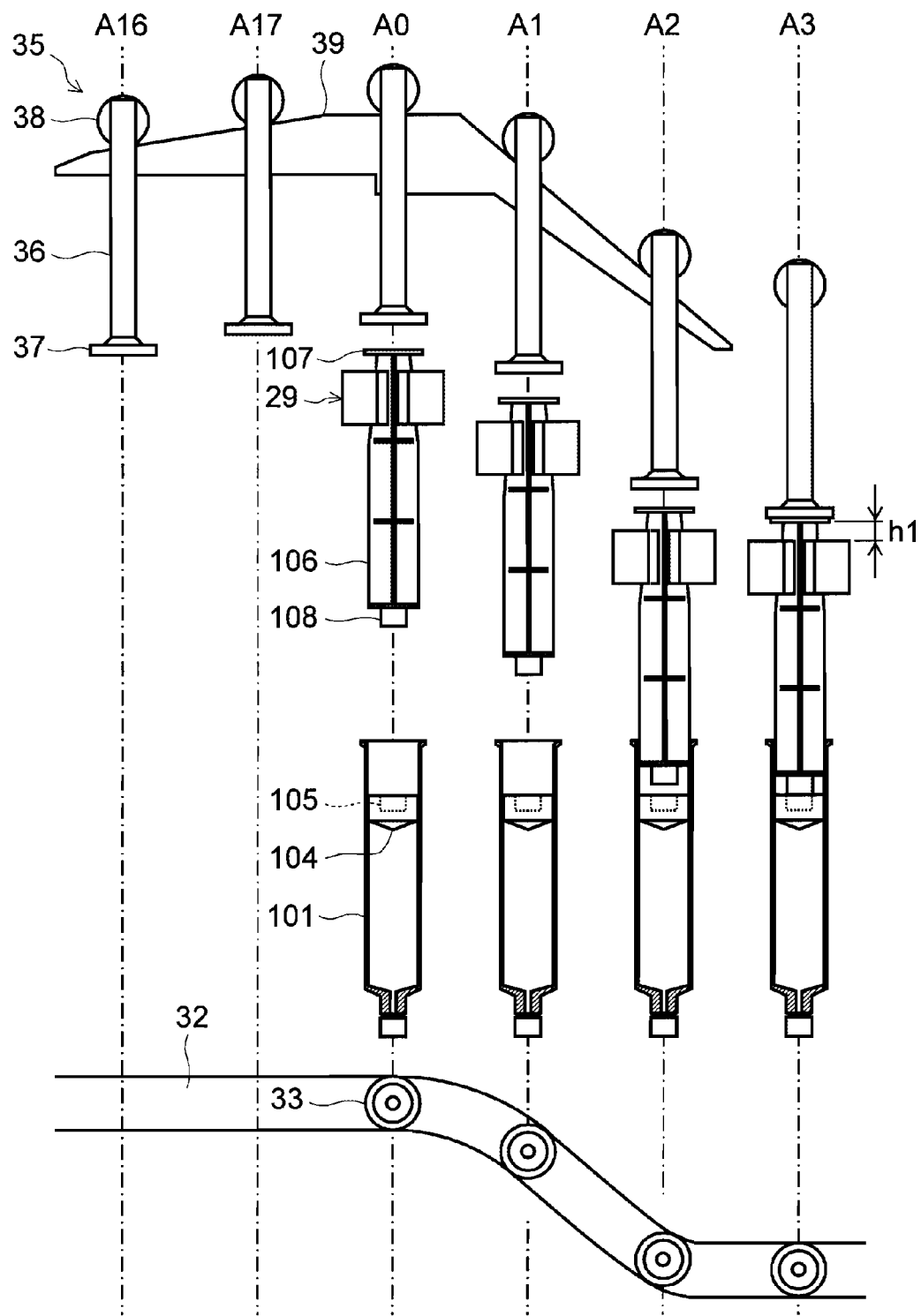
[FIG. 7] A first diagram for showing a syringe assembly process.

As shown in FIG. 7, at the angular position A0, the chuck 29 of the plunger rod support device 26 is raised high by the cam groove 32. The load application device 35, in which the cam follower 38 rides on the three-dimensional cam 39 before the angular position A16, is raised high by the three-dimensional cam 39 at the angular position A0. Here, the barrel support device 22 receives the barrel 101 from the component-receiving turret 10, and the plunger rod support device 26 receives the plunger rod 106 from the component-receiving turret 10. At first, the chuck 29 is in the full-open state shown in FIG. 3 and then, as soon as the plunger rod 106 is inserted, the chuck 29 is brought to the first holding state shown in FIG. 4, with the result that the chuck 29 firmly holds the plunger rod 106.

As the angular position transfers from A0 to A1 to A2 and to A3, the chuck 29 that pinches the plunger rod 106 in the first holding state is lowered. In the meantime, the end (lower end) of the plunger rod 106 is inserted into the barrel 101. This is the first operation of the plunger rod support device 26. At the angular position A2, the chuck 29 changes its state from the first holding state to the second holding state. Consequently, the plunger rod 106 cannot rotate about the axis but can slide down from the chuck 29. Even if the plunger rod 106 can slide down from the chuck 29, the plunger rod 106 is unlikely to drop down in a stroke to the place where the screw portion 108 makes contact with the screw portion 105 of the gasket 104, and the plunger rod 106 stays part way toward the place.

Here, the load application device 35, which has been lowered together with the chuck 29, leaves the three-dimensional cam 39 at a position between the angular positions A2 and A3, and places, on the plunger rod 106, a load exerted by a mass of the load application device 35 and acting in the downward direction along the axis of the plunger rod 106. Consequently, the plunger rod 106 is forcibly lowered until the screw portion 108 makes contact with the screw portion 105. This is the second operation of the plunger rod support device 26. After the second operation, a space h1 is left between the lower surface of the knob 107 of the plunger rod 106 and the upper surface of the chuck 29. In the load application device 35, a spring can be used as load application means instead of or in addition to its mass.

While the barrel support device 22 maintains the original height, and the chuck 29 maintains the height given by the chuck lifting device 34 at the angular position A3, they move to the angular position A9. The rotation application device 60 advances the rollers 62 toward three barrels 101 present at the angular positions A3, A4 and A5, respectively, and flexibly presses the rollers 62 onto the barrels 101 with an unillustrated spring. In this state, the rotation application device 60 moves along with the syringe assembly turret 20, and uses the motor 61 to drive the rollers 62, and thereby rotates the barrels 101. The direction of the rotation is the direction in which the screw portion 105 of the gasket 104 is screwed into the screw portion 108 of the plunger rod 106.

Figure 8:
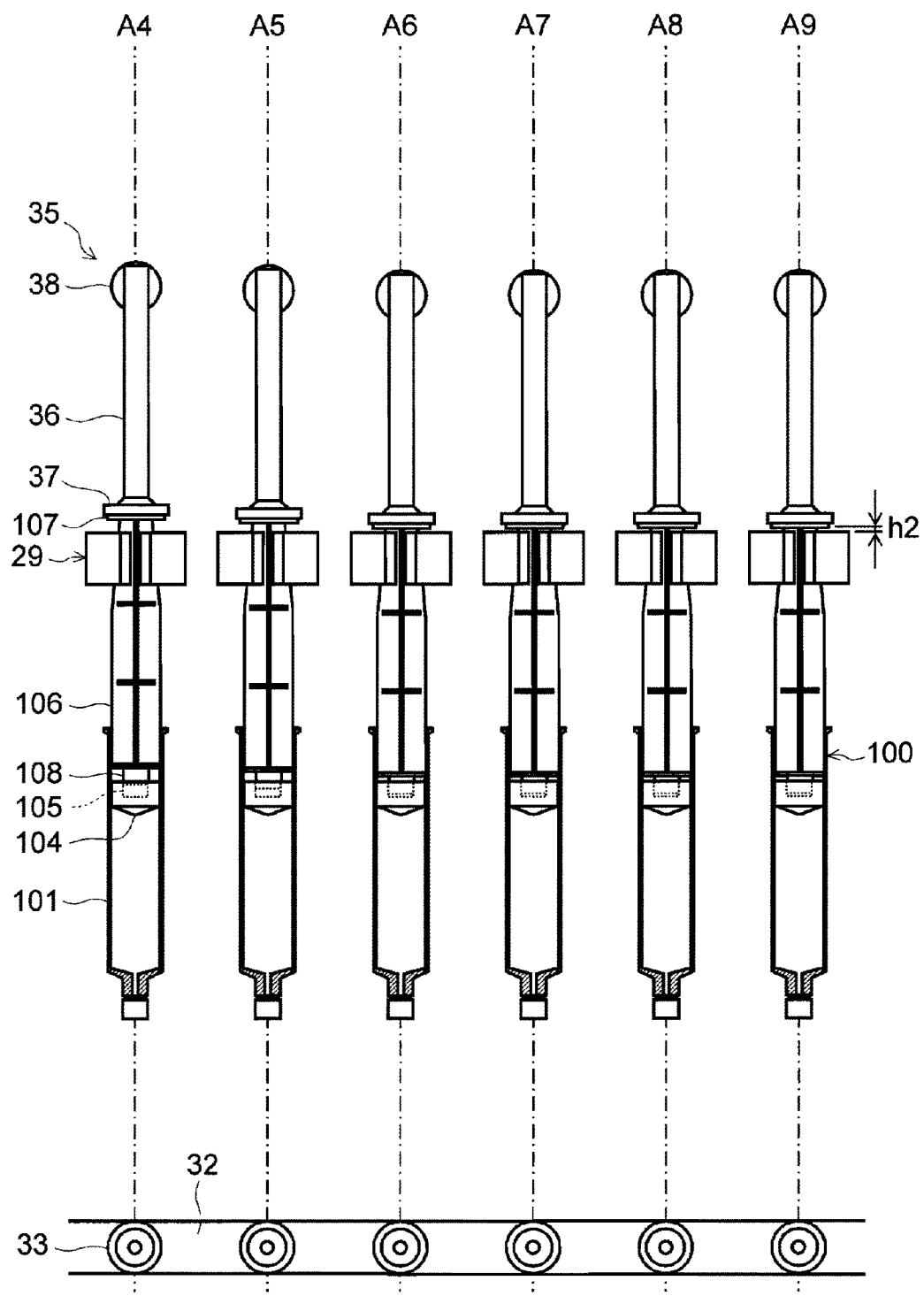
[FIG. 8] A second diagram for showing the syringe assembly process.

As the screwing is being performed, the plunger rod 106 that is prevented from rotating about its axis by the chuck 29 is lowered. How the plunger rod 106 is lowered is shown in FIG. 8. When, in each of the three barrels 101, the screw portion 105 is completely screwed into the screw portion 108, a torque for the screwing reaches a set torque value. The motors 61 that reach the set torque value individually stop the rotation. The torque at which the motor 61 stops the rotation, that is, the set torque value is set to the highest of the values at which relative rotation does not occur between the barrel 101 and the gasket 104. Thus, it is possible to prevent the case where the gasket 104 is forcibly rotated and thus the outer circumferential surface thereof is worn by friction with the inner surface of the barrel 101.

As described above, the load application device 35 is used to place the load acting axially and downwardly on the plunger rod 106, and simultaneously the rotation application device 60 is used to rotate the barrel 101 and thereby screw the plunger rod 106 into the gasket 104. Thus, as the screwing is being performed, the plunger rod 106 is naturally lowered, and the movement of the screw portion 105 of the gasket 104 that lowers the plunger rod 106 by a lead angle thereof does not differ from the actual movement of the plunger rod 106, resulting in complete and accurate screwing.

Moreover, when the chuck 29 is in the second holding state where the plunger rod 106 is prevented from rotating about the axis but is not prevented from sliding along its axis, the load application device 35 is used to place the load acting axially and downwardly on the plunger rod 106, and simultaneously the rotation application device 60 is used to rotate the barrel 101 and thereby screw the plunger rod 106 into the gasket 104, with the result that the screwing is performed without the plunger rod 106 being hindered from lowering When the screw portion 105 is completely screwed into the screw portion 108, the barrel 101, the gasket 104 and the plunger rod 106 are assembled into the syringe 100. Although the space between the lower surface of the knob 107 and the upper surface of the chuck 29 is reduced to a space h2 (see FIG. 8), the knob 107 still does not make contact with the chuck 29. Since this space h2 makes allowance, it is possible to accommodate variations in the depth by which the gasket 104 is inserted into the barrel 101.

Before the three barrels 101, which are originally placed in the angular positions A3, A4 and A5, reach the angular positions A6, A7 and A8, respectively, by advancing three angular positions, the rotary shuttle 50 reverses the direction of the movement, and then the rotary shuttle 50 returns to the positions where it receives barrels 101 that are newly supplied to the angular positions A3, A4 and A5. Here, the rollers 62 are pulled back against the force of the spring, and thus the rotary shuttle 50 does not make contact with the barrels 101 to rotate them while it is returning.

Even when parameters necessary to completely perform the screwing, such as the rotation angle of the barrel 101 and the outer diameter of the barrel 101, are changed, the change can be easily and conveniently dealt with by changing the control program of the motors 61 of the rotation application device 60.

Figure 9:
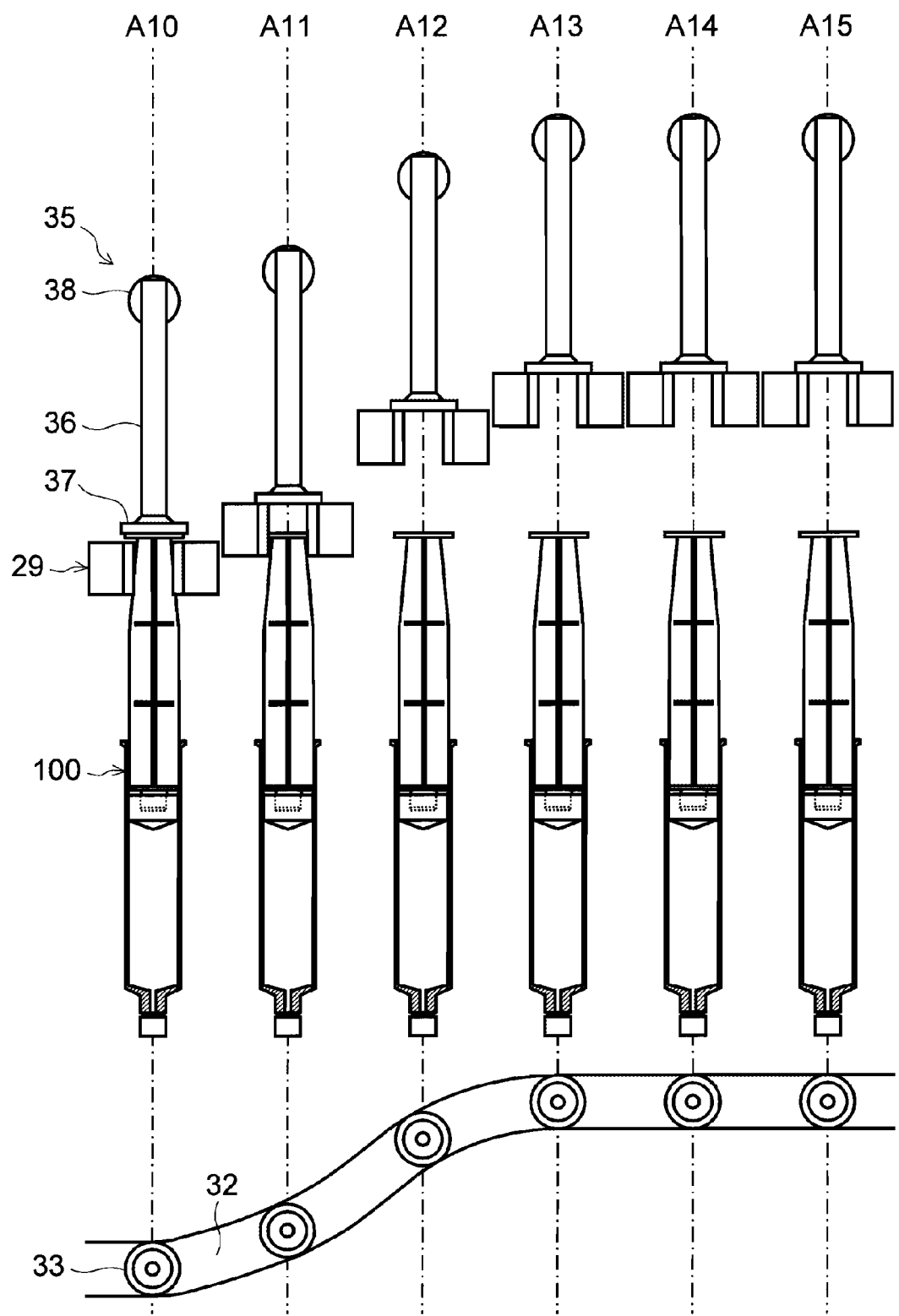
[FIG. 9] A third diagram for showing the syringe assembly process.

As shown in FIG. 9, when the chuck 29 reaches the angular position A10, it enters the full-open state. As the chuck 29 advances angular position positions, from A10 to A10 to A12 and to A13, the chuck 29 is raised to leave the syringe 100. The chuck 29 in the full-open state allows the knob 107 of the plunger rod 106 to pass therethrough but does not allow the pressure head 37 to pass therethrough, with the result that the load application device 35 is raised by the chuck 29. The chuck 29 reaches the highest height at the angular position A13, and moves from the angular position A14 to the angular position A15 without changing the height, and then makes the cam follower 38 ride on the three-dimensional cam 39 at the angular position A16.

When the syringe 100 passes through the angular position A15, the syringe 100 switches from the syringe assembly turret 20 to the relay turret 40. A fixed guide similar to the fixed guide 25 prevents the syringe 100 from coming off the relay turret 40. The relay turret 40 transfers the syringe 100 to the unillustrated label attachment line at a point where the relay turret 40 rotates about one half turn from the syringe receiving point.

The embodiment of the present invention is described above, and the scope of the invention is not limited to this embodiment, and many modifications are possible without departing from the scope of the invention. The numbers and values mentioned in this specification are simply examples, and the present invention is not limited to them.

What is claimed is:

1. A syringe assembly device, that performs, in a process of assembling a barrel, a gasket within the barrel and a plunger rod to be combined with the gasket into a syringe, a step of screwing the plunger rod into the gasket, the syringe assembly device comprising:
    a barrel support device that supports the barrel rotationally about an axis of the barrel at a predetermined height with the axis being arranged vertically and an opening of the barrel through which the plunger rod is inserted being directed upward;
    a plunger rod support device that includes: a chuck which pinches the plunger rod and holds the plunger rod above the opening of the barrel with an axis of the plunger rod being arranged vertically; and a load application device which places a load on the plunger rod held by the chuck; and
    a rotation application device that rotates the barrel about the axis of the barrel,
    wherein the load application device places the load acting axially and downwardly on the plunger rod which is held by the chuck and whose end is inserted into the barrel, and, in this state, the load application device rotates the barrel in a direction in which the plunger rod is screwed into the gasket.

2. The syringe assembly device of claim 1,
    wherein the chuck can enter a first holding state in which the plunger rod is prevented from rotating about and sliding along the axis of the plunger rod or a second holding state in which the plunger rod is prevented from rotating about the axis of the plunger rod but is not prevented from sliding along the axis,
    the plunger rod support device performs a first operation of lowering the chuck pinching the plunger rod in the first holding state to insert the end of the plunger rod into the barrel and a second operation of making the chuck enter the second holding state and making the load application device place the load acting axially and downwardly on the plunger rod, and the rotation application device rotates the barrel when the plunger rod support device performs the second operation.

3. The syringe assembly device of claim 1, wherein the barrel support device and the plunger rod support device are each provided in a plurality, and the barrel support devices and the plunger rod support devices are both spaced at equal angles on a circumference of a turret that rotates about a vertical axis, a chuck lifting device provided for the chuck includes: a three-dimensional cam arranged along a circling track of the plunger rod support device; and a chuck support stem being held by the turret such that the chuck support stem moves vertically along an undulation of the three-dimensional cam, the rotation application device is supported by a rotary shuttle that moves back and forth on an arc track having a same center as the turret; and each of the turret, the rotary shuttle and the rotation application device is driven by an individual motor.

* * * * *